United States Patent
Mathur et al.

(10) Patent No.: US 11,672,216 B2
(45) Date of Patent: Jun. 13, 2023

(54) METHODS FOR PROMOTING PRODUCTION OF VIABLE SEEDS FROM APOMICTIC GUAYULE PLANTS

(71) Applicant: American Biorubber, LLC, Solana Beach, CA (US)

(72) Inventors: Eric Jan Mathur, Encinitas, CA (US); Brett Tyler Roberts, San Diego, CA (US)

(73) Assignee: AMERICAN BIORUBBER, LLC, Solana Beach, CA (US)

( * ) Notice: Subject to any disclaimer, the term of this patent is extended or adjusted under 35 U.S.C. 154(b) by 256 days.

(21) Appl. No.: 16/721,385

(22) Filed: Dec. 19, 2019

(65) Prior Publication Data

US 2020/0120885 A1   Apr. 23, 2020

Related U.S. Application Data

(63) Continuation of application No. 15/571,001, filed as application No. PCT/US2016/029850 on Apr. 28, 2016, now abandoned.

(60) Provisional application No. 62/156,148, filed on May 1, 2015.

(51) Int. Cl.
| | |
|---|---|
| *A01H 1/02* | (2006.01) |
| *C08J 5/02* | (2006.01) |
| *A01H 6/14* | (2018.01) |
| *A01H 5/02* | (2018.01) |

(52) U.S. Cl.
CPC ............ *A01H 1/022* (2021.01); *A01H 1/02* (2013.01); *A01H 5/02* (2013.01); *A01H 6/14* (2018.05); *C08J 5/02* (2013.01); *C08J 2321/02* (2013.01)

(58) Field of Classification Search
CPC ..................................................... A01H 1/022
See application file for complete search history.

(56) References Cited

U.S. PATENT DOCUMENTS

| | | |
|---|---|---|
| 5,811,636 A | 9/1998 | Hanna et al. |
| 6,239,327 B1 | 5/2001 | Grossniklaus et al. |
| 7,442,850 B2 | 10/2008 | Wu et al. |
| 7,638,680 B2 | 12/2009 | Carman |
| 2014/0033342 A1 | 1/2014 | Gutterson et al. |
| 2014/0325699 A1 | 10/2014 | Kang et al. |
| 2020/0123565 A1 | 4/2020 | Schmidt et al. |

FOREIGN PATENT DOCUMENTS

WO   WO 2015/193733 A2 * 12/2015   ............ A01H 1/022

OTHER PUBLICATIONS

Ray, D.T. et al Industrial Crops and Products vol. 22, pp. 15-25 (Year: 2005).*
Estilai, A. Crop Science vol. 26, pp. 1261-1262 (Year: 1986).*
Hashemi et al Genome vol. 32, No. 1, pp. 134-140 (Year: 1989).*
West et al Bulletin of the Torrey Botanical Club vol. 115, No. 4, pp. 290-296 (Year: 1988).*
Gore, Michael A. et al., "Complex Ploidy Level Variation in Guayule Breeding Programs" Crop Science, Jan.-Feb. 2011, pp. 210-216, vol. 51.
Keys, Roy N. et al., "Characterization of Apomictic Potential in Guayule (*Parthenium argentatum*) In Vivo and In Vitro" J. Amer. Soc. Hort. Sci., 2002, pp. 404-408, vol. 127, No. 3.
Ray, Dennis T. et al., "Parent-Offspring Relationships in Apomictic Guayule" JAOCS, Dec. 1993, pp. 1235-1237, vol. 70, No. 12.
Ray, Dennis T. et al., "Breeding guayule for commercial production" Industrial Crops and Products, 2005, pp. 15-25, vol. 22.
International Search Report for PCT/US2016/029850 dated Aug. 12, 2016.
Larkin, P.J. et al. "Somaclonal Variation—a Novel Source of Variability from Cell Cultures for Plant Improvement" Theoretical and Applied Genetics, 1981, pp. 197-214, vol. 60.
Coffelt et al. "100 Years of Breeding Guayule". Handbook of Plant Breeding vol. 9. 251-367. (Year: 2014).
Keys and Ray. "Characterization of Apomictic Potential in Guayule (*Parthenium argentatum*) In Vivo and In Vitro". Journal of American Horticultural Science. 127(3):404-408. (Year: 2002).
Dong et al. "Overexpression of 3-hydroxy-3-methylglutaryl coenzyme A reductase in *Parthenium argentatum* (guayule)". Industrial Crops and Products. 46:15-24. (Year: 2013).
Thompson and Ray. "Breeding Guayule". Chapter 4; Plant Breeding Reviews vol. 6: 93-158. (Year: 1989).
Ray et al. "Registration of Six Guayule Germplasms with High Yielding Ability". Crop Science. 39: 300. (Year: 1999).
Camadro and Peloquin "Cross-incompatibility between two sympatric polyploidy *Solanum* species". Theor. Appl. Genet. 60: 65-70. (Year: 1981).
Scheben and Hojsgaard "Can we Use Gene-Editing to Induce Apomixis in Sexual Plants?". Genes 11(7): 1-28 (Year: 2020).

* cited by examiner

*Primary Examiner* — David H Kruse
(74) *Attorney, Agent, or Firm* — Frederic Dorwart Lawyers, PLLC; Penina Michlin

(57) ABSTRACT

Described herein are methods for producing guayule seeds, guayule plants, and products generated therefrom. More specifically, the disclosure provides methods for the production of viable seeds from apomictic guayule plants, seeds produced by such methods, plants grown from such seeds, plant parts, biomass, and biomaterials derived therefrom.

19 Claims, 4 Drawing Sheets

METHODS FOR PROMOTING PRODUCTION OF VIABLE SEEDS FROM APOMICTIC GUAYULE PLANTS

RELATED APPLICATIONS

This application is a Continuation of and claims the benefit and priority to U.S. patent application Ser. No. 15/571,001, filed on Oct. 31, 2017, which is a U.S. National Phase Application of PCT International Application Number PCT/US2016029850, filed on Apr. 28, 2016, designating the United States of America and published in the English language, which is an International Application of and claims the benefit of priority to U.S. Provisional Application No. 62/156,148, filed on May 1, 2015. The disclosures of the above-referenced applications are hereby expressly incorporated by reference in their entireties.

FIELD

The present disclosure generally relates to the field of agriculture, in particular to guayule seeds and methods for producing them. In particular, the disclosure provides methods for the production of viable seeds from guayule plants, including apomictic guayule plants. Seeds produced by such methods, plants grown from such seeds, plant parts, biomass, and biomaterials derived therefrom are also provided.

BACKGROUND

Guayule (*Parthenium argentatum* A. Gray), a member of the family Compositae (Asteraceae), is a desert shrub indigenous to the southwestern United States and northern Mexico. Guayule has been long-recognized as a particularly promising alternative source of natural rubber because of its potential for industrial-scale cultivation in the arid and semi-arid environments, and because the rubber harvested from it shows unusual hypoallergenic properties. It is generally believed that the economics of guayule production will improve significantly if higher-yielding lines can be developed using reliable and rapid methods of selecting plants with the best possible traits that will be passed faithfully to their progeny. (Ray et al., *Industrial Crops and Products*, 22:15-25, 2005).

Guayule has been readily manipulated by plant breeders for improvement because there exists many strains of wide genetic diversity with chromosome numbers of individual plants ranging from 2n=36 to 100 or more. However, perhaps the biggest challenge in developing commercial grade guayule hybrids through current plant breeding programs is the highly complex reproduction biology of this crop plant which is associated with its facultative nature of apomixis (e.g. asexual reproduction and sexuality coexisting). In fact, due to the facultative nature of apomixis in guayule, wild stands of this crop typically contain a natural polyploid series of diploids, triploids, and tetraploids; and under cultivation, individual plants have been identified with chromosome numbers up to octaploid (2N=8x=144). While diploids can reproduce predominantly sexually, they have had only limited use in current guayule breeding programs because they are largely self-incompatible. Triploids and pentaploids are known to also occur in guayule but, from a breeding point of view, these individuals are considered dead ends because they are reproduce predominantly through apomixis and produce very little viable pollen. Therefore, although some triploids and pentaploids have been documented as having relatively high latex content, these were generally not pursued for commercial latex production because a production field consisting of only apomictic triploids or pentaploids, albeit productive in terms of latex, may have been unproductive in terms of seeds for subsequent plantation expansion.

As a result, most existing guayule germplasm consists primarily of facultatively apomictic reproducing tetraploid accessions, which have received most of the attention in breeding programs. However, the process of inbreeding of tetraploid parent lines often time can be very consuming, especially because apomixis and sexuality coexist in these individuals. In fact, due to the facultative nature of apomixis in tetraploids, four classes of progeny generally exist. The origin and relative chromosome numbers of these four classes from tetraploid parents, as will be discussed in further detail herein, illustrates the complexity of reproduction and the potential for release of genetic variability in this species. In addition, the high amount of heterozygosity in individual plants and the heterogeneous make-up of guayule populations often results in the release of considerable variation whenever sexual reproduction occurs. Consequently, most of the guayule varieties currently used in large-scale production lack genetic uniformity.

Thus, there is a long-standing and continuing need for new methods for optimizing guayule breeding strategies for producing uniform hybrid progeny with agronomically desirable genotypes. This and other needs are discussed by the present disclosure.

SUMMARY

This section provides a general summary of the disclosure, and is not comprehensive of its full scope or all of its features.

Some alternatives disclosed herein relate to methods for promoting the production of viable hybrid guayule seeds from an interploidy cross. The methods include selecting a female guayule plant and a pollinator plant, wherein the female guayule plant is apomictic and the pollinator plant is capable of producing fertile pollen; pollinating the female guayule plant with pollen from the pollinator plant to produce seeds on the apomictic female guayule plant, where at least 5%, 10%, 15%, 20%, 25%, 30%, 35%, 40%, 45%, 55%, 60%, 70%, 80%, 90%, 95%, or 100% of the hybrid seeds are viable or where the percentage of viable hybrid seeds produced are within a range defined by any two of the aforementioned percentages. In some alternatives, the percentage of viable hybrid seeds is scored at 35 days after germination.

In some alternatives, the pollinator plant is a tetraploid guayule plant. In some alternatives, the female guayule plant is selected from a triploid guayule plant, a pentaploid guayule plant, and a heptaploid guayule plant. In some alternatives, the female guayule plant and said pollinator plant belong to the same *Parthenium* species. In some alternatives, the *Parthenium* species is *Parthenium argentatum*. In some alternatives, the female guayule plant and the pollinator plant belong to two different *Parthenium* species. In certain alternatives, the female guayule plant is a *Parthenium argentatum* plant. In some alternative, the pollinator plant is of a species selected from the group consisting of *P. alpinum, P. argentatum, P. cineraceum, P. confertum, P. fruticosum, P. hysterophorus, P. incanum, P. integrifolium, P. ligulatum, P. rollinsianum, P. schottii*, and *P. tomentosum*. In some alternatives, the pollinator plant is a *Parthenium argentatum* plant or a *Parthenium incanum* plant. In some alternatives, the pollinator plant is of a *Parthenium* species that is different than *Parthenium argentatum* such that any F1 hybrid off-types can be conveniently identified. In some alternatives, the pollinator plant is of a *Parthenium* species that is different than *Parthenium argentatum* such that F1 hybrid off-types can be conveniently identified based on inheritance of leaf morphological differences from the respective pollinator plants. In some alternatives, at least one of the female guayule plant or the pollinator plant is pre-selected for enhanced plant productivity. In some alternatives, at least one of the female guayule plant or the pollinator plant is clonally propagated prior to pollination step.

Some alternatives disclosed herein relate to methods for producing hybrid guayule seeds from an interploidy cross between female guayule plants from at least one female guayule line and pollinator plants from at least one pollinator plant line, in which the hybrid seeds having a percentage of viability above a predetermined percentage of viability. The methods include selecting the at least one female guayule line and the at least one pollinator plant line; determining a production ratio of female plants to pollinator plants to produce hybrid seeds having a percentage of viability above said predetermined percentage of viability; planting the at least one female guayule line and the at least one pollinator plant line in pollinating proximity in the production ratio in a production field; and allowing pollination of at least one of the female guayule plants with pollen from at least one of the pollinator plants, whereby the hybrid guayule seeds are produced. In certain alternative, the methods further include harvesting the hybrid guayule seeds.

In some alternatives, the female guayule plants include plants from a single female line. In some alternatives, the female guayule plants include plants from a plurality of female lines. In some alternatives, the at least one of said guayule female lines is a cloned apomictic guayule line. In some alternatives, the pollinator plants include plants from a single pollinator line. In some alternatives, the pollinator plants include plants from a plurality of pollinator lines. In some alternatives, the predetermined percentage of viability is 5%, 10%, 15%, 20%, 25%, 30%, 35%, 40%, 45%, 55%, 60%, 70%, 80%, 90, 95%, or 100%, or wherein the predetermined percentage of viability is within a range defined by any two of the aforementioned percentages. In some alternatives, the percentage of viable hybrid seeds is scored at 35 days after germination. In some alternatives, the production ratio of female plants to pollinator plants ranges from 10:1 to 1:5. In some alternatives, the production ratio of female plants to pollinator plants is 5:1, 4:1, 3:1, 2:1, or 1:1 or within a range defined by any two of the aforementioned ratios. In some alternatives, the selecting of at least one pollinator plant line includes selecting a pollinator line having high self-incompatibility or high production of viable pollen. In some alternatives, the planting includes planting the female guayule plants and the pollinator plants in multiple rows, in which each row of pollinator plants is interspersed with a plurality of rows of female guayule plants. In some alternatives, the plurality of rows of female guayule plants is 2 to 5 rows.

Some alternatives of the disclosure relate to viable hybrid guayule seeds produced by a method disclosed herein. In some alternatives, the viable plant seeds are produced by selecting a female guayule plant and a pollinator plant, wherein the female guayule plant is apomictic and the pollinator plant is capable of producing fertile pollen; pollinating the female guayule plant with pollen from the pollinator plant to produce seeds on the apomictic female guayule plant, where at least 5%, 10%, 15%, 20%, 25%, 30%, 35%, 40%, 45%, 55%, 60%, 70%, 80%, 90%, 95%, or 100% of the hybrid seeds are viable or where the percentage of viable hybrid seeds produced are within a range defined by any two of the aforementioned percentages. In some alternatives, the viable plant seeds are produced from an interploidy cross between female guayule plants from at least one female guayule line and pollinator plants from at least one pollinator plant line, in which the hybrid seeds having a percentage of viability above a predetermined percentage of viability. In some alternatives, the viable plant seeds are produced by (i) selecting at least one female guayule line and at least one pollinator plant line; (ii) determining a production ratio of female plants to pollinator plants to produce hybrid seeds having a percentage of viability above said predetermined percentage of viability; (iii) planting the at least one female guayule line and the at least one pollinator plant line in pollinating proximity in the production ratio in a production field; and (iv) allowing pollination of at least one of the female guayule plants with pollen from at least one of the pollinator plants, whereby the hybrid guayule seeds are produced.

Some alternatives disclosed herein relate to plants grown from the hybrid guayule seeds described herein. In some alternatives, the plants further include a transgene. In some alternatives, the transgene confers a trait selected from the group consisting of: abiotic stress tolerance, biotic stress tolerance, disease resistance, high latex yield, high overall rubber yield, high productivity, high resin yield, improved nitrogen use efficiency, improved water use efficiency, and plant vigor, or any combination of the aforementioned traits. Some alternatives relate to seeds, reproductive tissues, vegetative tissues, plant parts, biomass, or progeny of a plant disclosed herein. In some alternatives, the part of the plant is selected from the group consisting of an anther, an axillary bud, a cell, an embryo, a female gametophyte, a filament, a flower, a inflorescence, a leaf, a male gametophyte, a meristem, an ovary, an ovule, a petal, a pistil, a pollen grain, a protoplast, a root, a seed, a sepal, a stamen, a stem, a stigma, a style, a terminal bud, a cell of said plant in culture, a tissue of said plant in culture, an organ, a cutting, an explant, and a callus.

Some alternatives disclosed herein relate to methods for producing a product, including obtaining a plant or parts thereof as described in the present disclosure. Also disclosed, in some alternatives, are plant derived-products that are produced by the methods disclosed herein. In some alternatives, the plant-derived product is selected from the group consisting of latex, resin, fatty acid triglycerides, terpenes, sesquiterpenes, and waxes.

Some alternatives disclosed herein relate to a latex product derived from the latex disclosed herein, wherein the latex product is selected from the group consisting of medical gloves, surgical gloves, elastic bands, elastic traps, condom, automobile tires, truck tires, airplane tires, and wet suits.

The foregoing summary is illustrative only and is not intended to be in any way limiting. In addition to the illustrative aspects, alternatives, and features described above, further aspects, alternatives, and features will become apparent by reference to the drawings and the following detailed description.

DETAILED DESCRIPTION OF THE DISCLOSURE

Figures 1, 2:
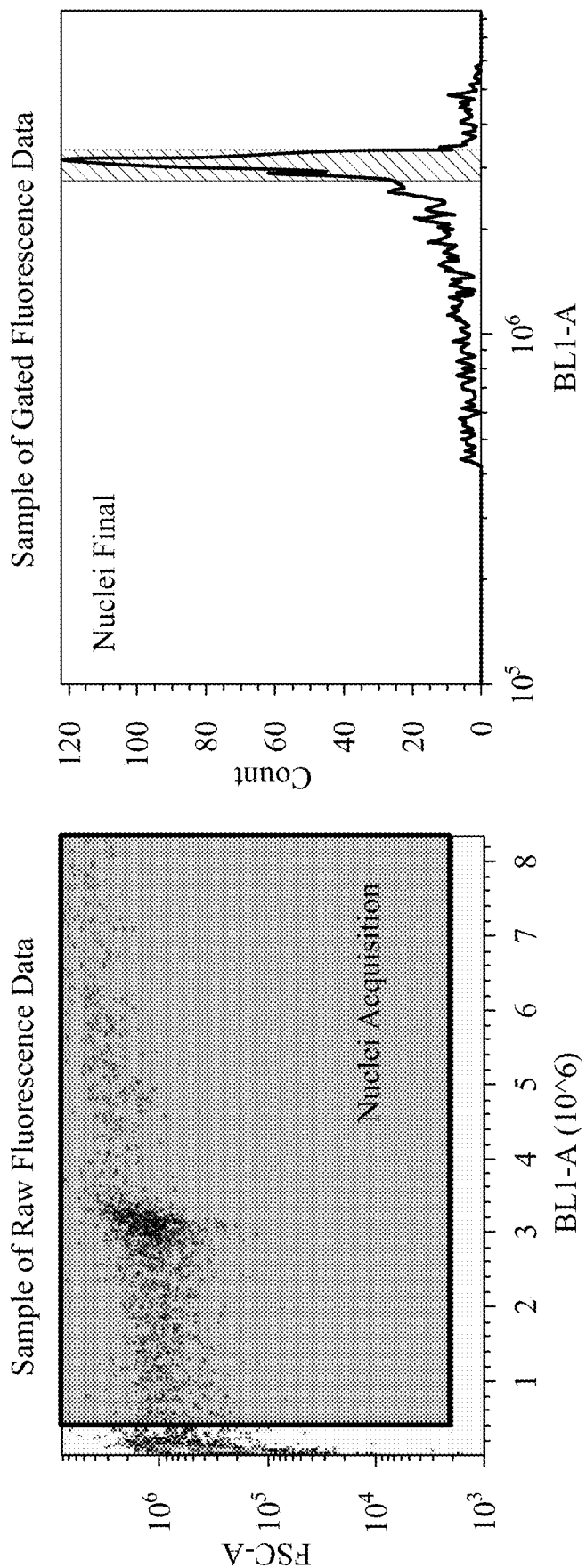
FIG. 1: Events recorded by the flow cytometer plotted by forward scatter (y-axis) and DNA fluorescence (x-axis). A nuclei gate was used to remove background debris from further analysis.
FIG. 2: Histogram of fluorescence values from gated events in FIG. 1. The gate provided the median fluorescence value for nuclei in the sample.

In the following detailed description, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Some Definitions

The singular form "a", "an", and "the" include plural references unless the context clearly dictates otherwise. For example, the term "a molecule" includes one or more molecules, including mixtures thereof. "A and/or B" is used herein to include all of the following alternatives: "A", "B", and "A and B".

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

"Apomixis", as used herein, in flowering plants is defined as the asexual formation of a seed from the maternal tissues of the ovule, avoiding the processes of meiosis and fertilization, leading to embryo development. All known mechanisms of apomixis share three developmental components: the generation of a cell capable of forming an embryo without prior meiosis (apomeiosis); the spontaneous, fertilization-independent development of the embryo (parthenogenesis); and the capacity to either produce endosperm autonomously or to use an endosperm derived from fertilization. As used herein, "obligate apomict" and grammatical equivalents thereof refer to a solitary plant that reproduces only by apomixis. The term "facultative apomict" and grammatical equivalents thereof refer to a solitary plant that reproduces both sexually and apomictically.

"Biomass": As used herein, plant biomass refers to the amount of (e.g., measured in grams of air-dry tissue) of a harvestable plant tissue produced from the plant in a growing season, which could also determine or affect the plant yield or the yield per growing area. Non-limiting examples of such harvestable plant tissues include leaves, stems, and reproductive structures, or all plant tissues such as leaves, stems, roots, and reproductive structures.

As used herein, the term "cultivar" or a "variety" refers to a group of similar plants that belong to the same species and that, by structural features and performance, may be distinguished from other varieties within the same species. Two essential characteristics of a variety are identity and reproducibility. Identity is necessary so that the variety may be recognized and distinguished from other varieties within the crop species. The distinguishing features may be morphological characteristics, molecular markers, color markings, physiological functions, disease reaction, or performance. Most agricultural varieties are pure for the characteristic or for those characteristics that identify the variety; per se. Reproducibility is needed in order that the characteristic(s) by which the variety is identified will be reproduced in the progeny. For the purpose of this disclosure, therefore, the terms "cultivar" and "variety" are used interchangeably to refer to a group of plants within a species (for example, *Parthenium argentatum*) that share certain constant characters which separate them from the typical form and from other possible varieties within that species. While possessing at least the distinctive trait, a "variety" of the disclosure also may be characterized by a substantial amount of overall variation between individuals within the variety, based primarily on the Mendelian segregation of traits among the progeny of succeeding generations. On the other hand, "cultivar" or "variety" also can denote a cloned line, because a *Parthenium argentatum* cultivar may individually be reproduced asexually, via stem cuttings, and all of the clones would be essentially identical genetically.

As used herein, a "line" refers to a population of plants derived from a single cross, backcross or selfing. The individual offspring plants are not necessarily identical to one another. As distinguished from a "variety," a "line" displays less variation between individuals, generally (although not exclusively) by virtue of several generations of self-pollination. For purposes of this disclosure, a "line" is defined sufficiently broadly to include a group of plants vegetatively or clonally propagated from a single parent plant, using stem cuttings or tissue culture techniques. "Vegetative propagation", as used herein, refers to asexual propagation of the plant that is accomplished by taking and propagating cuttings, by grafting or budding, by layering, by division of plants, or by separation of specialized structure, such as stem, roots, tubers, rhizomes, or bulbs.

The term "breeding line", as used herein, refers to a line of a cultivated crop having commercially valuable or agronomically desirable characteristics, as opposed to wild varieties or landraces. The term includes reference to an elite breeding line or elite line, which represents a line of plants used to produce commercial F1 hybrids. An elite breeding line is obtained by breeding and selection for superior agronomic performance comprising a multitude of agronomically desirable traits.

The term "hybrid", as used herein, refers to any offspring of a cross between two genetically non-identical individuals. The parental plants may be related, as in production of a modified single cross, or unrelated. F1 hybrid, as used herein, refers to the first generation progeny of the cross of two genetically dissimilar plants.

As used herein, the expressions "latex content", "rubber content", and "resin content" refer to the amount of latex, rubber, and resin respectively, in a given plant organ or tissue, such as the stem and is typically expressed as percentage of dry weight (for example at 10% humidity of biomass) or wet weight. It should be noted that latex, rubber, and resin content is affected by intrinsic latex, rubber, and resin production of a tissue (e.g., stem, leaf), as well as the mass or size of the latex-producing tissue per plant or per growth period. In some alternatives, increase in latex, rubber, or resin content of the plant can be achieved by increasing the size/mass of a plant's tissue(s) which contains latex, rubber, and resin per growth period. Thus, increased latex, rubber, and/or resin content of a plant can be achieved by increasing the yield, growth rate, biomass and vigor of the plant.

The term "plant part" refers to any part of a plant including, but not limited to, organelles, single cells and cell tissues such as plant cells that are intact in plants, cell clumps and tissue cultures from which guayule plants can be regenerated. Examples of plant parts include, but are not limited to, single cells and tissues from pollen, ovules, leaves, embryos, roots, root tips, tubers, anthers, flowers, fruits, stems shoots, and seeds; as well as pollen, ovules, leaves, embryos, roots, root tips, anthers, flowers, fruits, stems, shoots, scions, rootstocks, seeds, tubers, protoplasts, and calli. The two main parts of plants grown in some sort of media, such as soil, are often referred to as the "above-ground" part, also often referred to as the "shoots", and the "below-ground" part, also often referred to as the "roots".

As used herein, "progeny" includes descendants of a particular plant or plant line. Progeny of an instant plant include seeds formed on F1, F2, F3, F4, F5, F6 and subsequent generation plants, or seeds formed on BC1, BC2, BC3, and subsequent generation plants, or seeds formed on F1BC1, FiBC2, FiBC3, and subsequent generation plants. The designation F1 refers to the progeny of a cross between two parents that are genetically distinct. The designations F2, F3, F4, F5 and F6 refer to subsequent generations of self- or sib-pollinated progeny of an F1 plant.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

The present disclosure generally describes methods for generating viable hybrid seeds from apomictic guayule plants. Seeds produced by such methods, plants grown from such seeds, plant parts, biomass, and biomaterials derived therefrom are also provided.

Apomixis

In angiosperms, two pathways of reproduction through seed exist: sexual or amphimictic and asexual or apomictic. The latter is largely exploited by seed companies for crop production and breeding new varieties, whereas the latter is receiving continuously increasing attention from both scientific and industrial sectors. The term apomixis is generally interpreted as the replacement of sexual reproduction by various forms of asexual reproduction. Mechanistically, apomixis is a genetically controlled reproductive method in plants where the embryo is formed without union of an egg and a sperm. (Bicknell and Koltunow, *Plant Cell*, Vol. 16, S228-245, 2004). Apomixis affects both megasporegenesis and megagametogenesis, but typically does not alter pollen formation. Meiosis still occurs normally in the anthers, and viable, reduced pollen is usually produced in both aposporous and diplosporous apomicts. There are three basic types of apomictic reproduction: 1) apospory-embryo develops from a chromosomally unreduced egg in an embryo sac derived from the nucellus, 2) diplospory-embryo develops from an unreduced egg in an embryo sac derived from the megaspore mother cell, and 3) adventitious embryony-embryo develops directly from a somatic cell. In most forms of apomixis, pseudogamy or fertilization of the polar nuclei to produce endosperm is necessary for seed viability. Apomixis is considered to be facultative when some progeny also result from either a normal meiosis and/or a normal fertilization of the egg cell, and as a result, a facultative apomictic plant can produce various frequencies of maternal progenies. Apomixis is considered to be obligate when the progeny is 100% maternal.

Apomixis has an important potential impact on agricultural and food production by reducing cost and breeding time, and avoiding the complications that are typical of sexual reproduction (for example, incompatibility barriers) and vegetative propagation (for example, viral transfer). In addition, in outcrossing species that reproduce sexually, alleles disseminate in the offspring; thus, the optimal genotype is lost together with the desired trait. In contrast, apomixis is a reproductive process that bypasses female meiosis and syngamy to produce embryos genetically identical to the maternal parent, and therefore apomixis can cause any genotype, regardless of how heterozygous, to breed true, e.g., progeny of highly adaptive or hybrid genotypes with apomictic reproduction would maintain their genetic fidelity throughout repeated life cycles. Therefore, the genotype of every apomictic would be fixed in the F1 generation and every apomictic genotype from a cross has the potential of being a cultivar. Gene combinations and vigor would not be lost as in each segregating generation of sexual F1 hybrids. The maintenance of elite genotypes would be therefore easier and more efficient. In addition to fixing hybrid vigor, apomixis can make possible commercial hybrid production in crops where efficient male sterility or fertility restoration systems for producing hybrids are not known or developed. Further, apomixis could have a major impact in commercial hybrid production systems by simplifying hybrid seed production and therefore making hybrid development more efficient.

Guayule

Guayule, a member of the family Compositae (Asteraceae), is a xerophytic, woody perennial shrub indigenous to the southwestern United States and northern Mexico. In addition to producing hydrocarbon rubber polymers during the winter (Cornish and Backhaus, *Industrial Crops and Products*, 17:83-92, 2003), guayule produces and stores a high-energy hydrocarbon terpenoid resin in specialized resin vessels throughout the year (Coffelt et al., *Industrial Crops and Products*, 29:255-260, 2009). Guayule (*Parthenium argentatum* Gray) is so named because of a silvery sheen on its gray-green leaves which are covered in a drought-protecting white wax. Guayule flowers are pollinated by wind and by insects. Guayule plant is generally a bushy perennial shrub with alternate narrow leaves along the stem. It bears a canopy inconspicuous, hardy and between two and three feet high. The plant generally can survive 30-40 years under desert conditions. Descriptions of guayule cultivation practices have been reviewed extensively by Thompson and Ray (*Plant Breed Rev.* 6:93-165, 1989) and Ray DT (*Guayule: A source of natural rubber*. p. 338-343. In: J. Janick and J. E. Simon (eds.), 1993, New Crops. Wiley, New York). Guayule has been long-recognized as a particularly promising alternative source of natural rubber and bioactive terpenoid compounds, because of its potential for industrial-scale cultivation in the arid and semi-arid environments, and because the rubber harvested from it shows unusual hypoallergenic properties. It is generally believed that the economics of guayule production will improve significantly if higher-yielding lines can be developed using reliable and rapid methods of selecting plants with the best possible traits that will be passed faithfully to their progeny. Ray et al., *J. Amer. Soc. Hort. Sci.* 132(2):213-218, 2007; (Ray et al., *Industrial Crops and Products*, 22:15-25, 2005).

However, perhaps the biggest challenge in developing commercial grade guayule hybrids through current plant breeding programs is the highly complex reproduction biology of this crop plant, which is associated with its facultative nature (e.g. apomixis and sexuality coexisting) and the high amount of heterozygosity in individual plants and the heterogeneous make-up of populations, resulting in the release of considerable variation whenever sexual reproduction (amphimixis) occurs. Most of the guayule varieties currently used in large-scale production are heterozygous at many loci and thus lack genetic uniformity. As such, a sexual cross between two genetically dissimilar parents typically results in a heterogeneous collection of F1 hybrids that not only segregate genotypically, but also show dramatic phenotypic differences. Further, the process of inbreeding of parent lines often time can be very consuming, especially because apomixis and sexuality coexist. In fact, diploid guayule plants reproduce predominantly sexually, and polyploids reproduce by facultative apomixis. Due to the facultative nature of guayule, wild stands of guayule typically contain a natural polyploid series of diploids ($2N=2x=36$), triploids ($2N=3x=54$) and tetraploids ($2N=4x=72$); and under cultivation, individual plants have been identified with chromosome numbers up to octaploid ($2N=8x=144$). Another reproductive feature is reported to occur frequently in polyploid guayule is haploidy, which is the reduction of chromosome number from, for example, 2N to 1N. In this instant, the egg cell has a reduced chromosome number because meiosis has occurred, but the stimulus for apomictic development still exists and the egg in the reduced condition produces a new haploid plant. In addition, to further complicate current breeding efforts, guayule also has a sporophytic system of self-incompatibility and many plants contain B- or supernumerary chromosomes (Ray et al. 2007, supra; Thompson and Ray, *Breeding guayule. Plant Breed Rev.*, 6:93-165, 1989).

Most existing guayule germplasm consists primarily of apomictically reproducing tetraploid accessions, which have received most of the attention in breeding programs. The tetraploid plants are generally much larger and more vigorous than the diploids, and they readily produce seeds through apomixis. Fields of primarily tetraploid plants could be used to not only produce latex/rubber but could also be used for seed production. Breeders have performed mass selections on tetraploid lines to identify individuals with higher latex/rubber yields. These can be propagated by cuttings or by the facultatively apomictic-derived seeds. However, the process of inbreeding of parent lines often time can be very consuming, especially because apomixis and sexuality coexist. In fact, the facultative nature of apomixis in tetraploid plants results in four classes of progeny. The origin and relative chromosome numbers of these four classes from tetraploid parents illustrates the complexity of reproduction and the potential for release of genetic variability in this species. The predominant class of progeny arises from non-reduction of the megaspore mother cell (MMC), without fertilization. These are apomictic tetraploid progeny and are identical generically to the maternal parent. Progeny from fertilized, unreduced MMCs include plants with increased ploidy levels. In this example, these progeny would be hexaploid ($2N=6x=108$). Polyhaploid ($2N=2x=36$) plants are the result of meiotic reduction of the tetraploid MMC, and embryo development without fertilization. The final class would be amphimictic tetraploid ($2N=4x=72$) progeny that arises from normal reduction and fertilization. Thus, there are two reproductive modes that produce tetraploid progeny, one by apomixis and the other by sexual reproduction. As a result, a plant breeder cannot easily differentiate between the apomictic and sexual progeny based on chromosome number alone. The remaining two progeny classes vary in chromosome number from the parental population and therefore can be identified relatively easy.

On the other hand, triploids and pentaploids are known to occur in guayule, but have had only limited use in current guayule breeding programs. Although some triploids and pentaploids have been documented as having a relatively high latex content, these were generally not pursued for commercial latex production because a field of only triploids or pentaploids, although productive in terms of latex, may have been unproductive in terms of seeds for subsequent plantation expansion. This is because, similar to other polyploids, triploid (3x) and pentaploid (5x) guayule reproduce apomictically. From a breeding point of view, these individuals are considered dead ends because they reproduce predominantly through apomixis and produce very little viable pollen. In the case of triploids, a small percentage of off-types, e.g., pentaploid (5x) seeds can also occur at low frequencies. Triploid and pentaploid guayule plants generally can produce flowers and set seed. However in the absence of fertile pollen from tetraploid (4x) pollinator, the endosperm development is defective and while many of the seeds apomictically produced by triploid and pentaploid guayule plants with unfertilized endosperm can germinate, none of the seedlings survive past day 30 after germination. From these studies, a method for generating viable seed was devised and disclosed herein.

As described in greater detail in the Examples below, Applicants have developed a breeding strategy that takes advantage of all these subtle reproductive nuances in guayule, and combines them into methods that permit the production of viable hybrid seeds from triploid and pentaploid guayule plants.

In particular, according to some alternatives disclosed herein, Applicants have demonstrated that the production of viable apomictic seed production in triploids and pentaploids require the presence of fertile pollen. While Applicants do not wish to be bound by any theory, it is believed that the presence of pollen from fertile plants, particularly tetraploid plants, help assure the completion of seed development in the apomictically produced seeds on triploid and pentaploid plants. While the embryo is not fertilized, pollen from fertile plants assures the fertilization of the polar nuclei and subsequent completion of the endosperm development in these apomictically produced seeds.

Seed Production Methods

In one aspect, some alternatives of the present disclosure relate to methods for promoting the production of viable hybrid guayule seeds from an interploidy cross. In some alternatives, the methods include a step of selecting a female guayule plant and a pollinator plant, where the female guayule plant is apomictic and the pollinator plant is capable of producing fertile pollen. Generally, the female plant can be any guayule plant capable of producing an embryo and can be, for example, a diploid guayule plant, a triploid guayule plant, a tetraploid guayule plant, a pentaploid guayule plant, a hexaploid guayule plant, a heptaploid guayule plant, or an octaploid guayule plant. In some preferred alternatives, the female plant can be selected from the group consisting of a triploid guayule plant, a pentaploid guayule plant, or and heptaploid guayule plant. In some particularly preferred alternatives, the female plant can be a triploid guayule plant. In some particularly preferred alternatives, the female plant can be a pentaploid guayule plant. In some alternative of the methods disclosed herein, the male pollinator plant can generally be any plant capable of producing fertile pollen. Non-limiting examples of suitable pollinator plants include a haploid guayule plant, a diploid guayule plant, a triploid guayule plant, a tetraploid guayule plant, a pentaploid guayule plant, a hexaploid guayule plant, a heptaploid guayule plant, or an octaploid guayule plant. In some preferred alternatives, the male pollinator can be a tetraploid guayule plant.

In some alternatives of the methods disclosed herein, a second step comprises pollinating the female guayule plant with pollen from the pollinator plant to produce seeds on the apomictic female guayule plant. In addition, this step can optionally comprise preventing self-pollination of the plants, e.g., preventing the ovules of a plant from being fertilized by pollen of the same plant or of any plant of the same plant cultivar or variety. This can be done, for example, by emasculating the flowers of the female plant, (e.g., treating or manipulating the flowers so as to prevent pollen production, in order to produce an emasculated parent female guayule plant). Self-incompatibility systems may also be used in some hybrid production schemes for the same purpose. Typically, self-incompatible plants still shed viable pollen and can pollinate plants of other varieties but are incapable of pollinating themselves or other plants of the same variety.

In some embodiments, the female guayule plant is pollinated with pollen from the pollinator plant to produce seeds on the apomictic female guayule plant in a manner that at least about 5%, at least about 10%, at least about 15%, at least about 20%, at least about 25%, at least about 30%, at least about 35%, at least about 40%, at least about 45%, at least about 55% of the hybrid seeds are viable. In some embodiments, the female guayule plant is pollinated with pollen from the pollinator plant to produce seeds on the apomictic female guayule plant in a manner that at least about 60%, at least about 70%, at least about 80%, at least about 90%, at least about 95%, or at least about 100% of the hybrid seeds are viable. In some embodiments, the female guayule plant is pollinated with pollen from the pollinator plant to produce seeds on the apomictic female guayule plant in a manner that the percentage of viable hybrid seeds produced are within a range defined by any two of the aforementioned percentages. In some particular alternatives of the methods disclosed herein, about 13% of the hybrid seeds are viable. In some alternatives, about 35% of the hybrid seeds are viable. In some alternatives, about 40% of the hybrid seeds are viable. In some alternatives, about 65% of the hybrid seeds are viable.

The percentage of viable hybrid seeds can be scored at different developmental stages and can be, for example, scored at 15, 20, 30, 40, 50 days after germinations. In some alternatives, the percentage of viable hybrid seeds is scored at 35 days after germination.

In principle, the methods disclosed herein can be deployed for the production of viable hybrid seeds of any *Parthenium* species. Suitable *Parthenium* species to be used include, but not limited to *P. alpinum, P. argentatum, P. cineraceum, P. confertum, P. fruticosum, P. hysterophorus, P. incanum, P. integrifolium, P. ligulatum, P. rollinsianum, P. schottii*, and *P. tomentosum*. Preferred *Parthenium* species include *Parthenium argentatum* or a *Parthenium incanum*. Particularly preferred *Parthenium* species to be used in the methods disclosed herein is *Parthenium argentatum*. Non-limiting examples of preferred *P. argentatum* varieties and cultivars include AZ-2, AZ-4, AZ-R2, AZ-11591, ARIZ-101, GH-9, UCR-7, UCR-1, USDA-10, USDA-5, USDA-7, ALI-10, USS2x, G-89, G-97, C-244, USDA Cal-6, USDA Cal-7, USDA-593, USDA-N565, and USDA-N396. Other non-limiting examples of preferred *P. argentatum* varieties and cultivars include YX-5-03-bLr-02 and YX-5-03-bLr-02 (Yulex Corp.). Other non-limiting examples of preferred *P. argentatum* varieties and cultivars include PA 11-2, PA 11-3, PA 11-4, PA 11-8, PA 10-4, PA 10-14, PA 10-16, PA 10-18, and PA 10-23 (Panaridus, LLC).

In some alternatives of the methods disclosed herein, the female guayule plant and the pollinator plant selected for the interploidy cross belong to the same *Parthenium* species. In some alternatives, the female guayule plant and the pollinator plant selected for the interploidy cross belong to different *Parthenium* species such that any F1 hybrid off-types from the interploidy cross can be conveniently identified. In some alternatives, the female guayule plant is a *Parthenium argentatum* plant. In some alternatives, the pollinator plant is of a species selected from the group consisting of *P. alpinum, P. argentatum, P. cineraceum, P. confertum, P. fruticosum, P. hysterophorus, P. incanum, P. integrifolium, P. ligulatum, P. rollinsianum, P. schottii*, and *P. tomentosum*. In some preferred alternatives, the pollinator plant is a *Parthenium argentatum* plant or a *Parthenium incanum* plant. In some particularly preferred alternatives, the female plant is a *Parthenium argentatum* plant and the pollinator plant is of a *Parthenium* species that is different than *Parthenium argentatum* such that any F1 hybrid off-types from the interploidy cross can be conveniently identified.

In some alternatives of the methods disclosed herein, at least one of the parental female plant and the male pollen donor can be pre-selected for enhanced plant productivity. As used herein, "enhanced plant productivity" refers to any aspect of a plant altered for a "desired benefit," such as increasing an agriculturally desirable trait. "Desired benefit" also refers to any effect on a plant to confer a benefit to humans. As used herein, "agriculturally desirable trait" refers to any qualitative and quantitative agricultural trait, such as high productivity, crop yield, biomass, resistance to pathogens, resistance to pests, resistance to environmental changes, for example, drought, etc. In other words, a desirable trait is any characteristic worth obtaining. In some alternatives, the guayule plants selected as described above are intercrossed with one another, followed by progeny testing to evaluate general combining abilities (intercrossability).

In some alternatives, at least one of the parental female plant and the male pollen donor can be clonally propagated prior to pollination step. The clonal propagation can generally be any known clonal propagation techniques and can be, for example, tissue-culture, rooted cutting, stem cutting, stake cutting, or any of other means of vegetative propagation.

In one aspect, some alternatives of the present disclosure relate to methods for producing hybrid guayule seeds from an interploidy cross between female guayule plants from at least one female guayule line and pollinator plants from at least one pollinator plant line, in which the hybrid seeds having a percentage of viability above a predetermined percentage of viability. In some alternatives, the methods include selecting the at least one female guayule line and the at least one pollinator plant line; determining a production ratio of female plants to pollinator plants to allow for production of hybrid seeds having a percentage of viability above said predetermined percentage of viability; planting the at least one female guayule line and the at least one pollinator plant line in pollinating proximity in the production ratio in a production field; and allowing pollination of at least one of the female guayule plants with pollen from at least one of the pollinator plants, whereby the hybrid guayule seeds are produced. The term "pollinating proximity" as used herein refers to the distance that two plants or two rows of plants can be planted from each other but can still cross-pollinate.

In some alternatives, selection of female guayule line and the pollinator plant line takes into account both agronomic factors and factors that affect percentage of intercrossability (e.g., general combining abilities), hybrid seed yield, and hybrid seed viability. The term "intercrossable", as used herein, refers to the ability to yield progeny plants after making crosses between parental plants. In some exemplary alternatives, these agronomic factors and factors include: female to pollinator ratio, seed yield from pollinator plants, seed yield from female plants, female to pollinator seed yield differential, female to pollinator seed size differential, high seed yield with increasing female to pollinator plant ratio, low P.P.I. (Pollen Production Index), large seed size, pollination power in pollinator plants, high production of viable pollen in pollinator plants, and high self-incompatibility in pollinator plants. In further aspects of the disclosure, these factors include desirable agronomic traits such as disease resistance, insect resistance, and abiotic stress resistance.

In certain alternative, the methods disclosed herein further include harvesting the hybrid guayule seeds.

In some alternatives, the female guayule plants include plants from a single female line. In some alternatives, the female guayule plants include plants from a plurality of female lines. In principle, the methods disclosed herein can generally include plants from any number of female lines and can include, for example, plants from at least 2, at least 3, at least 4, at least 5, at least 6, at least 7, at least 8, at least 9, at least 10 female lines. In some alternatives, the at least one of said guayule female lines is a cloned apomictic guayule line, e.g. a line including guayule plants vegetatively or clonally propagated from a single parent plant, using stem cuttings or tissue culture techniques. In some alternatives, the pollinator plants include plants from a single pollinator line. In some alternatives, the pollinator plants include plants from a plurality of pollinator lines. Generally, the methods can include plants from any number of female lines and can include, for example, plants from at least 2, at least 3, at least 4, at least 5, at least 6, at least 7, at least 8, at least 9, at least 10 pollinator lines. In some alternatives, the predetermined percentage of viability is 5%, 10%, 15%, 20%, 25%, 30%, 35%, 40%, 45%, 55%, 60%, 70%, 80%, 90, 95%, or 100%, or wherein the predetermined percentage of viability is within a range defined by any two of the aforementioned percentages. In some alternatives, the percentage of viable hybrid seeds is scored at 35 days after germination. In some alternatives, the production ratio of female plants to pollinator plants ranges from 10:1 to 1:5. In some alternatives, the production ratio of female plants to pollinator plants is 5:1, 4:1, 3:1, 2:1, or 1:1 or within a range defined by any two of the aforementioned ratios. In some alternatives, the selecting of at least one pollinator plant line includes selecting a pollinator line having high self-incompatibility or high production of viable pollen. In some alternatives, the planting includes planting the female guayule plants and the pollinator plants in multiple rows, in which each row of pollinator plants is interspersed with a plurality of rows of female guayule plants. The plurality of rows of female guayule plants can generally, 16 rows of be any number of rows and can be, for example, 2, 3, 4, 5, 6, 7, 8, 9, 10, 11, 12, 13, 14, 15 rows of female guayule plants, or within a range defined by any two of the aforementioned. For example, in some alternatives, the plurality of rows of female guayule plants can be 2 to 10 rows, 5 to 15 rows, 3 to 9 rows, 4 to 8 rows, 5 to 10 rows. In some alternatives, the plurality of rows of female guayule plants can be 2 to 5 rows.

In one aspect, some alternatives of the present disclosure relate to viable hybrid guayule seeds that are produced by a method in accordance with some alternatives disclosed herein.

In a related aspect, some alternatives of the present disclosure relate to a guayule plant that is grown from a seed produced by a method in accordance with some alternatives disclosed herein. As use herein, phrases such as "grown from the seed" or "grown the seed" include techniques and practices known in the art including, but are not limited to, embryo rescue, isolation of cells from seed for use in tissue culture, as well as traditional growing methods. Descriptions of current guayule cultivation practices have been reviewed extensively. Information in this regard can be found in, for example, Thompson and Ray (*Breeding guayule*. Plant Breed Rev. 6:93-165, 1989, and in *Guayule Natural Rubber*, edited by Whitworth and Whitehead (1991).

As used herein, the term "tissue culture" refers to a composition comprising isolated plant cells of the same or a different type or a collection of such cells organized into parts of a plant, in which the cells are propagated in a nutrient medium under controlled conditions. Non-limiting examples of tissue cultures include plant protoplasts, plant cell tissue culture, culture microspores, plant calli, plant clumps, and the like.

In one aspect, the present disclosure further provides a seed, a reproductive tissue, a vegetative tissue, a plant part, a biomass, or progeny of a guayule hybrid plant disclosed herein. In some alternatives of this aspect, provided herein is a plant part of a guayule hybrid plant disclosed herein, wherein the plant part is selected from the group consisting of an anther, an axillary bud, a cell, an embryo, a female gametophyte, a filament, a flower, a inflorescence, a leaf, a male gametophyte, a meristem, an ovary, an ovule, a petal, a pistil, a pollen grain, a protoplast, a root, a seed, a sepal, a stamen, a stem, a stigma, a style, a terminal bud, a cell of said plant in culture, a tissue of said plant in culture, an organ, a cutting, an explant, and a callus.

Genetically Engineered Guayule Plants

In some alternatives of the disclosure, the guayule plants disclosed herein can include a transgene. The advent of new molecular biological techniques has allowed the isolation and characterization of genetic elements with specific functions, such as sequences encoding specific protein products or sequences having promoter activity. Scientists in the field of plant biology developed a strong interest in engineering the genome of plants to contain and express foreign genetic elements, or additional, or modified versions of native or endogenous genetic elements in order to alter the traits of a plant such as, a guayule plant disclosed herein, in a specific manner. Any heterologous DNA sequences, whether from a different species or from the same species which are inserted into the genome using genetic transformation, are referred to herein collectively as "transgenes".

Plant transformation involves the construction of an expression vector which will function in plant cells. Such a vector typically comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed guayule plants, using transformation methods as described below to incorporate transgenes into the genetic material of the guayule plant(s).

Accordingly, in some alternatives of the disclosure, the guayule plants disclosed herein can include a transgene can be inserted in a nucleic acid construct which is maintained and replicated in the guayule plant as an episomal unit. In some alternatives, the transgene is stably integrated into the genome of the guayule plant. Stable integration can be completed using classical random genomic recombination techniques, homologous recombination, or with more precise genome editing techniques such as using guide RNA directed CRISPR/Cas9 or TALEN genome editing. In some alternatives, the transgene is present in the guayule plant disclosed herein as a mini-circle expression vector for a stable or transient expression.

A transgene can be introduced into a guayule plant of the present disclosure by a variety of techniques. These techniques, able to transform a wide variety of higher plant species including guayule plants, are known and described extensively in the technical and scientific literature. For examples, a number of methods for plant transformation, which have been previously developed for the genetic transformation of various plant species, can be deployed for the transformation of guayule. See, for example, Mild et al., "*Procedures for Introducing Foreign DNA into Plants*" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are readily available. See, for example, Gruber et al., "*Vectors for Plant Transformation*" in Methods in Plant Molecular Biology and Biotechnology, Glick B. R. and Thompson, J. E. Eds. (CRC Press, Inc., Boca Raton, 1993) pp. 89-1 19. Suitable genetic transformation methods include electroporation (U.S. Pat. No. 5,384,253), micro-projectile bombardment (Sanford, J. C, *Physiol Plant* 7:206, 1990; Sanford I., *Part. Sci. Technol.* 5:27, 1987; Sanford J. C, Trends Biotech. 6:299, 1988; Klein et al., *BioTechnology* 6:559-563, 1988; Klein, et al., *Biotechnology* 10:268, 1992; U.S. Pat. Nos. 5,538,880; 5,550, 318; 5,736,369; and PCT Patent Pub. No. WO 95/06128), *Agrobacterium*-mediated transformation (Moloney, et al., *Plant Cell Reports* 8:238, 1989; Horsch et al., *Science* 227: 1229, 1985; Kado, *Crit. Rev. Plant Sci.* 10: 1, 1991; U.S. Pat. Nos. 5,563,055; 5,591,616; and EP Pat. Pub EP672752), direct DNA uptake transformation of protoplasts (Omirulleh et al., *Plant Mol. Biol*, 21(3):415-428, 1993), and silicon carbide fiber-mediated transformation (U.S. Pat. Nos. 5,302, 532 and 5,464,765).

More specifically, methods for the genetic transformation of guayule are known to those of skill in the art. See, e.g., Dong et al., *Plant Cell Rep.*, 25(1):26-34, 2006; U.S. Pat. No. 8,013,213; Veatch et al., *Ind. Crop Prod.*, 22:65-74. 2005. In particular, guayule has been successfully transformed to express several genes involved in the synthesis of terpenoid precursors; mono-, sesqui- and di-terpenoid molecules; and isoprenoid rubber polymers using *Agrobacterium*-mediated transformation (Veatch et al., *Industrial Crops and Products*, 22:65-74, 2005). Further, methods have been developed for the optimal extraction of resin and terpenoid moieties from harvested guayule tissues (Pearson et al., *Industrial Crops and Products*, 31:469-475, 2010; Salvucci et al., *Industrial Crops and Products*, 30:9-16, 2009). Moreover, transgenic guayule lines have been successfully brought to field trials, where they have been demonstrated to accumulate increased accumulations of terpenoid-rich resins (Veatch et al., 2005).

Additional technical details related to materials, systems and methods useful for genetic transformation of guayule, including selectable markers, suitable promoters, and expression vectors, have been previously documented in, e.g., Li et al., *Plant Cell Tissue Organ Cult.* 92: 173-181, 2008; Khemkladngoen et al., *Plant Biotechnol. Rep.* 5:235-243, 2011; Kumar et al., *Ind. Crops Prod.* 32:41-47, 2010; and Tsuchimoto et al., *Plant Biotechnol.* 29: 137-143, 2012; US Pat. Pub. Nos. US20060217512 and US20060218660, each of which is incorporated herein by reference in its entirety.

Transformed seeds, plants, plant cells, and plant parts obtained by such transformation methods are intended to be within the scope of this disclosure. Following transformation of guayule target tissues, expression of a suitable selectable marker gene allows for preferential selection of transformed cells, tissues and/or plants, using regeneration and selection methods known in the art. In addition, seeds obtained from the transformed plants can be used for testing stability and inheritance. Generally, two or more generations are cultivated to ensure that the phenotypic feature is stably maintained and transmitted. A person of ordinary skill in the art will recognizes that after a transgene is stably incorporated in transgenic plants and confirmed to be operable, it can be introduced into other plants by sexual crossing.

Accordingly, in some alternatives of the present disclosure, a guayule hybrid plant disclosed herein can contain at least one transgene. In some alternatives, a guayule hybrid plant disclosed herein can contain at least 2, 3, 4, 5, 6, 7, 8, 9, 10 transgenes and/or no more than 15, 14, 13, 12, 11, 10, 9, 8, 7, 6, 5, 4, 3, or 2 transgenes.

In addition or alternatively, in some alternatives of the disclosure, various genetic elements can be introduced into the plant genome using transformation techniques. These elements include, but are not limited to genes, coding sequences, inducible, constitutive, and tissue specific promoters, enhancing sequences, and signal and targeting sequences. For example, see the traits, genes and transformation methods listed in Pan et al., *Plant Cell, Tissue and Organ Culture,* 46:2, 143-150, 1996; Dong et al., *Plant Cell Rep.,* 25: 1, 26-34, 2006; Veatch et al., *Ind. Crop Prod.,* 22:65-74. 2005; and U.S. Pat. No. 8,013,213.

It will be understood by those of skill in the art that a transgene need not be directly transformed into a plant, as techniques for the production of stably transformed guayule plants that pass single loci to progeny by Mendelian inheritance is well known in the art. Such loci may therefore be passed from parent plant to progeny plants by standard plant breeding techniques that are well known in the art. Thus, the foregoing methods for transformation would typically be used for producing a transgenic variety. The transgenic variety could then be crossed with another (non-transformed or transformed) variety, in order to produce a new transgenic variety. Alternatively, a genetic trait which has been engineered into a particular guayule variety using the foregoing transformation techniques could be moved into another variety using traditional backcrossing techniques that are well-known in the plant breeding arts. For example, a backcrossing approach could be used to move an engineered trait from a public, non-elite variety into an elite variety, or from a variety containing a foreign gene in its genome into a variety or varieties which do not contain that gene.

Some alternatives of the present disclosure further provide a process for producing a guayule plant that further comprises a desired trait. The process comprises transforming a guayule plant provided herein with a transgene that confers a desired trait. In some related alternatives, the disclosure provides a transformed guayule plant produced by this process, and seeds produced by such transformed plants. In yet some other alternatives, the desired trait may be one or more of: abiotic stress tolerance, biotic stress tolerance, disease resistance, high latex yield, high overall rubber yield, high productivity, high resin yield, improved nitrogen use efficiency, improved water use efficiency, and plant vigor, or any combination of the aforementioned traits. The specific genes useful for this process may be any gene known in the art for its ability to confer such traits. Non-limiting examples of such trait genes include genes encoding various allylic diphosphate synthases in the rubber biosynthesis pathway, including geranylgeranyl pyrophosphate synthase (GGPP); hexa-heptaprenyl pyrophosphate synthase, and farnesyl pyrophosphate synthase (FPP) (U.S. Pat. No. 8,013,213); Veatch et al., *Ind. Crop Prod.,* 22:65-64. 2005; Dong et al., *Plant Cell Rep,* 25: 1, 26-34, 2006.

In a related aspect, some alternatives disclosed herein relate to seeds, plants, plant cells and plant parts disclosed herein further comprising a transgene. In some alternatives, the disclosure further provides seeds, reproductive tissues, vegetative tissues, plant parts, biomass, or progeny of a plant according to the present disclosure.

Products Derived from Guayule Plants

Further provided, in one aspect of the present disclosure, is a method for producing a plant-derived product. The method according to this aspect of the disclosure includes obtaining a hybrid plant grown from a hybrid seed produced by any of the foregoing methods, or a part thereof, and producing said plant-derived product therefrom.

Accordingly, additionally provided, in another aspect of the present disclosure, is a plant product produced by a process of producing a plant-derived product disclosed herein. In some alternatives of this aspect, the plant derived-product is selected from the group consisting of latex, resin, fatty acid triglycerides, terpenes, sesquiterpenes, or waxes. Methods and systems useful for the production of resins derived from plant species bearing rubber and rubber-like hydrocarbons have been previously reported. In addition, methods and systems useful for preparation and utilization of multi-component copolymers of guayule resin with improved physical and chemical properties are also well documented. Information in this regard can be found in, for example, Ray, D. T. 1993. Guayule: *A source of natural rubber,* p. 338-343. In: J. Janick and J. E. Simon (eds.), New Crops. Wiley, New York; Estilai et al., *Developing guayule as a domestic rubber crop,* California Agriculture, Sep.-Oct. 29-30, 1988; Ray et al., *Industrial Crops Products,* 22: 15-25, 2005; Veatch et al., *Ind. Crop Prod.,* 22:65-64. 2005; Dong et al., *Plant Cell Rep.,* 25: 1, 26-34, 2006; U.S. Pat. Pub. Nos. US20060218660, US20090163689, US20060217512, US20090099309, PCT Pat. Pub. Nos. WO2007081376, WO2007136364, and WO2008147439, U.S. Pat. Nos. 5,717,050; 7,259,231; 5,580,942; 7,790,036; and 8,013,213; each of which is incorporated herein by reference in its entirety.

In some preferred alternatives of this aspect, the plant derived-product is further defined as a latex product. In some particularly preferred alternatives, the latex product is selected from the group consisting of medical gloves, surgical gloves, elastic bands, elastic traps, condom, automobile tires, truck tires, airplane tires, and wet suits.

In some alternatives, products such as latex, resin, fatty acid triglycerides, terpenes, sesquiterpenes, or waxes can be recovered from the hybrid plants of the present disclosure by recovery means known to those skilled in the art.

All publications and patent applications mentioned in this specification are herein incorporated by reference to the same extent as if each individual publication or patent application was specifically can individually indicated to be incorporated by reference.

Throughout this disclosure, various information sources are referred to and are, where specifically noted, incorporated by reference. While the contents and teachings of each and every one of the information sources can be relied on and used by one of skill in the art to make and use alternatives of the disclosure, any discussion and comment in a specific information source should in no way be considered as an admission that such comment was widely accepted as the general opinion in the field.

The discussion of the general methods given herein is intended for illustrative purposes only. Other alternative methods and aspects will be apparent to those of skill in the art upon review of this disclosure, and are to be included within the spirit and purview of this application.

Headings within the application are solely for the convenience of the reader, and do not limit in any way the scope of the disclosure or its alternatives. Additional alternatives include the following embodiments:

1. A method for promoting the production of viable hybrid guayule seeds from an interploidy cross, said method comprising:

selecting a female guayule plant and a pollinator plant, wherein said a female guayule plant is apomictic and said pollinator plant is capable of producing fertile pollen;

pollinating said female guayule plant with pollen from said pollinator plant to produce seeds on said apomictic female guayule plant, wherein at least 5%, 10%, 15%, 20%, 25%, 30%, 35%, 40%. 45%, 55%, 60%, 70%, 80%, 90%, or 95% of said hybrid seeds are viable or wherein the percentage of viable hybrid seeds produced are within a range defined by any two of the aforementioned percentages.

2. The method of alternative 1, wherein said pollinator plant is a tetraploid guayule plant.

3. The method of alternative 1 or 2, wherein said female guayule plant is selected from a triploid guayule plant, a pentaploid guayule plant, or a heptaploid guayule plant.

4. The method of any one of alternatives 1-3, wherein said female guayule plant and said pollinator plant belong to the same *Parthenium* species.

5. The method of alternative 4, wherein said *Parthenium* species is *Parthenium argentatum*.

6. The method of any one of alternatives 1-3, wherein said female guayule plant and said pollinator plant belong to two different *Parthenium* species.

7. The method of any one of alternatives 1-6, wherein said female guayule plant is a *Parthenium argentatum* plant.

8. The method of any one of alternatives 1-7, wherein the pollinator plant is of a species selected from the group consisting of *P. alpinum, P. argentatum, P. cineraceum, P. confertum, P. fruticosum, P. hysterophorus, P. incanum, P. integrifolium, P. ligulatum, P. rollinsianum, P. schottii*, and *P. tomentosum*.

9. The method of any one of alternatives 1-8, wherein said pollinator plant is a *Parthenium argentatum* plant or a *Parthenium incanum* plant.

10. The method of any one of alternatives 1-9, wherein at least one of said female guayule plant or said pollinator plant is pre-selected for enhanced plant productivity.

11. The method of any one of alternatives 1-10, wherein at least one of said female guayule plant or said pollinator plant is clonally propagated prior to pollination step.

12. The method of any one of alternatives 1-11, wherein said pollinator plant is of a *Parthenium* species that is different than *Parthenium argentatum* such that any F1 hybrid off-types from said interploidy cross can be conveniently identified.

13. The method of any one of alternatives 1-12, wherein said percentage of viable hybrid seeds is scored at 35 days after germination.

14. A method for producing hybrid guayule seeds from an interploidy cross between female guayule plants from at least one female guayule line and pollinator plants from at least one pollinator plant line, said hybrid seeds having a percentage of viability above a predetermined percentage of viability, said method comprising:

selecting said at least one female guayule line and said at least one pollinator plant line;

determining a production ratio of female plants to pollinator plants to produce hybrid seeds having a percentage of viability above said predetermined percentage of viability;

planting said at least one female guayule line and said at least one pollinator plant line in pollinating proximity in said production ratio in a production field; and allowing pollination of at least one of said female guayule plants with pollen from at least one of said pollinator plants, whereby said hybrid guayule seeds are produced.

15. The method of alternative 14, further comprising harvesting said hybrid guayule seeds.

16. The method of alternative 14 or 15, wherein said female guayule plants comprise plants from a single female line.

17. The method of alternative 14 or 15, wherein said female guayule plants comprise plants from a plurality of female lines.

18. The method of any one of alternatives 14-17, wherein at least one of said guayule female lines is a cloned apomictic guayule line.

19. The method of any one of alternatives 14-18, wherein said pollinator plants comprise plants from a single pollinator line.

20. The method of any one of alternatives 14-18, wherein said pollinator plants comprise plants from a plurality of pollinator lines.

21. The method of alternative 14, wherein the predetermined percentage of viability is 5%, 10%, 15%, 20%, 25%, 30%, 35%, 40%. 45%, 55%, 60%, 70%, 80%, 90, 95%, or 100% or wherein the predetermined percentage of viability is within a range defined by any two of the aforementioned percentages.

22. The method of any one of alternatives 14-21, wherein said percentage of viable hybrid seeds is scored at 35 days after germination.

23. The method of any one of alternatives 14-22, wherein said production ratio of female plants to pollinator plants ranges from 10:1 to 1:5.

24. The method of alternative 23, wherein said production ratio of female plants to pollinator plants is 5:1, 4:1, 3:1, 2:1, or 1:1 or within a range defined by any two of the aforementioned ratios.

25. The method of any one of alternatives 14-25, wherein said selecting at least one pollinator plant line comprises selecting a pollinator line having high self-incompatibility or high production of viable pollen.

26. The method of any one of alternatives 14-26, wherein said planting comprises planting said female guayule plants and said pollinator plants in multiple rows, wherein each row of pollinator plants is interspersed with a plurality of rows of female guayule plants.

27. The method of alternative 26, wherein said plurality of rows of female guayule plants is 2 to 5 rows.

28. A hybrid guayule seed produced by a method of any one of alternatives 1-27.

29. A viable hybrid guayule seed produced by:

selecting a female guayule plant and a pollinator plant, wherein said a female guayule plant is apomictic and said pollinator plant is capable of producing fertile pollen;

pollinating said female guayule plant with pollen from said pollinator plant to produce seeds on said apomictic female guayule plant, wherein at least 5%, 10%, 15%, 20%, 25%, 30%, 35%, 40%. 45%, 55%, 60%, 70%, 80%, 90%, or 95% of said hybrid seeds are viable or wherein the percentage of viable hybrid seeds produced are within a range defined by any two of the aforementioned percentages.

30. Viable hybrid seeds produced from an interploidy cross between female guayule plants from at least one female guayule line and pollinator plants from at least one pollinator plant line, said hybrid seeds having a percentage of viability above a predetermined percentage of viability, wherein said hybrid seeds produced by:

selecting said at least one female guayule line and said at least one pollinator plant line;

determining a production ratio of female plants to pollinator plants to produce hybrid seeds having a percentage of viability above said predetermined percentage of viability;

planting said at least one female guayule line and said at least one pollinator plant line in pollinating proximity in said production ratio in a production field; and allowing pollination of at least one of said female guayule plants with pollen from at least one of said pollinator plants, whereby said hybrid guayule seeds are produced.

31. A plant grown from the hybrid guayule seed of any one of alternatives 28-30.

32. The plant of alternative 31, further comprising a transgene.

33. The plant of alternative 32, wherein said transgene confers a trait selected from the group consisting of: abiotic stress tolerance, biotic stress tolerance, disease resistance, high latex yield, high overall rubber yield, high productivity, high resin yield, improved nitrogen use efficiency, improved water use efficiency, plant vigor, and combinations of at least two of the aforementioned traits.

34. A seed, a reproductive tissue, a vegetative tissue, a plant part, a biomass, or a progeny of a plant according to any one of alternatives 31-33.

35. A plant part of alternative 34, wherein said plant part is selected from the group consisting of an anther, an axillary bud, a cell, an embryo, a female gametophyte, a filament, a flower, a inflorescence, a leaf, a male gametophyte, a meristem, an ovary, an ovule, a petal, a pistil, a pollen grain, a protoplast, a root, a seed, a sepal, a stamen, a stem, a stigma, a style, a terminal bud, a cell of said plant in culture, a tissue of said plant in culture, an organ, a cutting, an explant, and a callus.

36. A method for producing a product, comprising obtaining a plant or parts thereof set forth in any one of alternatives 31-35.

37. A plant derived-product produced by the method of alternative 36.

38. The plant-derived product of alternative 37, which is selected from the group consisting of latex, resin, fatty acid triglycerides, terpenes, sesquiterpenes, and waxes.

39. A latex product derived from the latex of alternative 38, wherein said latex product is selected from the group consisting of medical gloves, surgical gloves, elastic bands, elastic traps, condom, automobile tires, truck tires, airplane tires, and wet suits.

EXAMPLES

Additional alternatives are disclosed in further detail in the following examples, which are not in any way intended to limit the scope of the claims.

Example 1

Production of Triploid Guayule Offspring Via 2×x4×Interploidy Pollination

This Example illustrates methods for producing triploid offspring via pollination of a diploid female guayule plant with pollen from a tetraploid pollen donor. In a first set of experiments, fluorescent flow cytometry was used to analyze the nucleic acid content and ploidy level of hybrid seeds derived from 2×x4×interploidy crosses. Flow cytometry has been used previously for cytological applications such as determination of ploidy levels, detection of aneuploidy, screening of reproductive mode, analysis of cell cycle, and estimation of absolute nuclear DNA amount (nuclear genome size). Compared to chromosome counting, flow cytometry is a rapid and simple method for the determination of ploidy levels in crop species. With a high level of accuracy, flow cytometry indirectly estimates the number of chromosomes in somatic cells by measuring the DNA content of fluorescence stained nuclei. Further information regarding applications of this technique in determination of guayule ploidy levels can be found in, for example, Gore et al., *Crop Science,* 51:210-216, 2011, hereby incorporated by reference in its entirety.

Four tetraploid and four diploid guayule plants were grown under standard greenhouse conditions until flowering. Each diploid plant was pruned of flowers and placed in isolation within a pollination cage together with one of the tetraploid plants. Blue bottle flies (genus *Calliphora*) were added weekly to the cages to facilitate pollination. Achenes were harvested from each diploid plant after thirty days of co-cultivation. The achenes were then germinated on a paper towel in a 15-cm petri dish with 20 ml of diH$_2$O. The petri dishes were sealed with parafilm and incubated in a growth chamber with a 14 hour day length, day temperature of 27° C. and night temperature of 22° C. for germination. The number of germinated seeds was scored at day 4, day 7, and day 14 of incubation. Seedlings were transferred to grow containers (Grodan™ blocks) a few days following germination.

After the seedlings were fully established in 4-inch pots, two 5-mm hole punches were sampled from each seedling in triplicate and placed into a 96-well microtube rack. Tissue was also collected from plants of diploid, triploid, and tetraploid plant controls and loaded on the microtube rack. A 3-mm carbide bead and 500 µL of Baranyi I solution (100 mM citric acid monohydrate; 0.5% (v/v) Triton X-100) were loaded into each well before disrupting the samples with a TissueLyser II solution (QIAGEN) at 27 Hz for 30 seconds. Nuclear lysates were then centrifuged through a 30-40 µm filter to remove cellular debris. Subsequently, two parts Baranyi II solution (400 mM Na$_2$HPO$_4$, 10 mM sodium citrate, 25 mM sodium sulfate) mixed with SYBR® Green I (Sigma-Aldrich) were added to one part of the nuclei extract to bring the final sample to 2×SYBR Green I and a neutral pH (7.0-8.0). Stained nuclei samples were allowed to incubate in the dark at room temperature for 30 minutes before analysis. The fluorescence value relative to the DNA content of nuclei for each sample was acquired using an Attune® Flow Cytometer (Life Technologies) and Attune® Autosampler (Life Technologies). An acquisition flow rate of 100 µl/min and an acquisition volume of 50 µl were used. Nuclei peaks were manually gated (FIGS. 1 and 2) and the resulting median fluorescence values were compared against intraspecific controls to generate ploidy callus.

Germination rates were scored after 35 days of incubation. As summarized in TABLE 1, the scored germination rates of seeds derived from 2×x4×interploidy crosses varied from 13.4% to 39.4%. The percentages of seedling survival after 35 days of the seedlings that germinated were 35.7% and 65.6%, respectively. Notably, a significant fraction of seedlings derived from the interploidy crosses, if not all seedlings, germinated within the first 7 days.

TABLE 1

Germination results from each diploid × tetraploid (2X × 4X) caged cross.
Achenes were collected from the diploid in each cross.

| Location | Cross | Number of Achenes Collected | Number of Achenes Germinated | | | Percent Germination | | | Seedling Survival @ Day 35 | |
|---|---|---|---|---|---|---|---|---|---|---|
| | | | Day 4 | Day 7 | Day 14 | Day 4 | Day 7 | Day 14 | Number | Percent |
| CAGE 2 | 2X × 4X | 71 | 20 | 28 | 28 | 28.2 | 39.4 | 39.4 | 10 | 35.7 |
| CAGE 3 | 2X × 4X | 170 | 32 | 45 | 45 | 18.8 | 26.5 | 26.5 | 25 | 55.5 |
| CAGE 4 | 2X × 4X | 175 | 32 | 40 | 40 | 18.3 | 22.9 | 22.9 | 18 | 45 |
| CAGE 5 | 2X × 4X | 239 | 30 | 30 | 32 | 12.6 | 12.6 | 13.4 | 21 | 65.6 |

Figure 3:
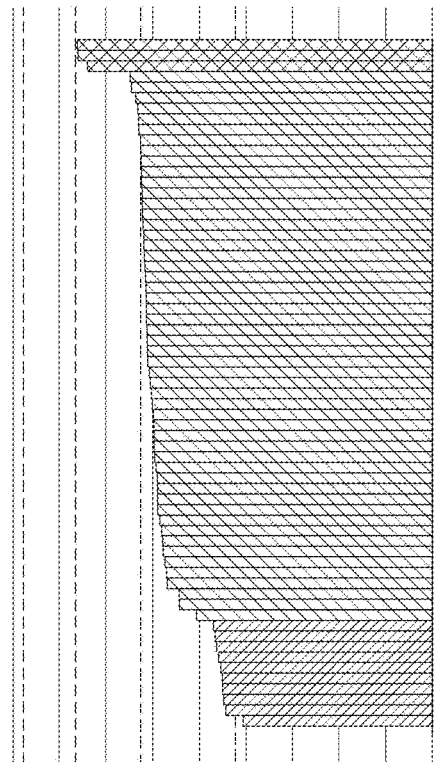
FIG. 3: Fluorescent values of nuclei samples acquired from the F1 seedlings of each caged cross. Values were ordered from left to right by increasing fluorescence regardless of replicate or seedling ID. Horizontal dotted lines represented median fluorescent values of intraspecific controls (diploid, triploid, tetraploid, pentaploid).
Figure 3:
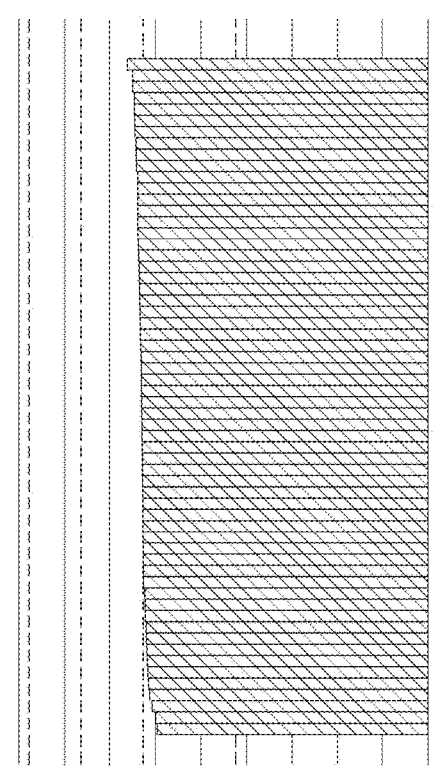
Figure 3:
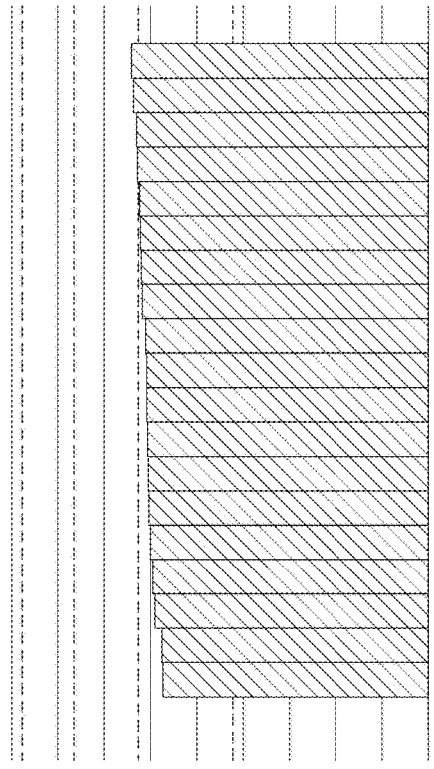
Figure 3:
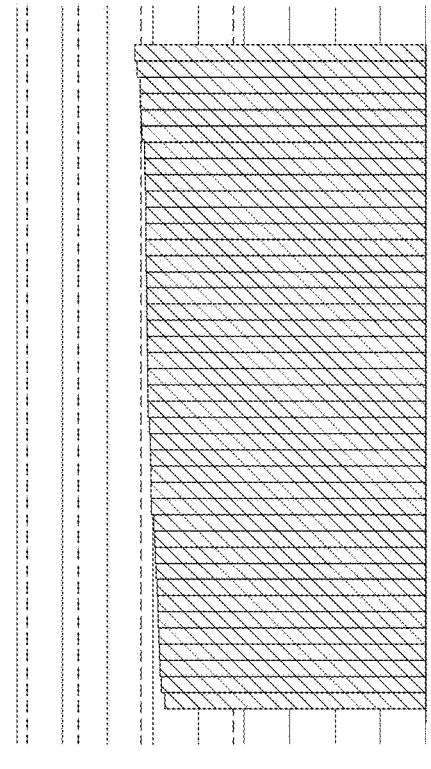

Fluorescence data acquired from each F1 seedling was plotted alongside data from other F1 seedlings of the same caged cross (FIG. 3). Each column represents a sample replicate corresponding to a particular F1 seedling. Values were ordered from lowest to highest fluorescence intensity and showed only small variation. Fluorescence values for the intraspecific controls are plotted as horizontal dotted lines. As shown in TABLE 2, three of the four 2x×4x interploidy crosses produced only triploid F1 seedlings. It was also observed that one of the crosses (Cage 3) produced 4 diploids, 18 triploids, and 1 tetraploid, as indicated by the fluorescence data plotted for Cage 3, which clearly showed separation between the seedling samples of different ploidy levels.

TABLE 2

Ploidy levels of the F1 seedlings derived from each of the four interploidy crosses.

| | F1 Seedlings | | | | |
|---|---|---|---|---|---|
| Location | Diploid, 2X | Triploid, 3X | Tetraploid, 4X | Total | % Hybrid |
| CAGE 2 | 0 | 7 | 0 | 7 | 100% |
| CAGE 3 | 4 | 18 | 1 | 23 | 78% |
| CAGE 4 | 0 | 16 | 0 | 16 | 100% |
| CAGE 5 | 0 | 20 | 0 | 20 | 100% |

Conclusions

The ploidy levels of the F1 seedlings from each caged cross indicated that pollination of a diploid female plant with pollen from a tetraploid pollen donor produced predominantly triploid (hybrid) offspring. While three out of the four caged crosses produced only triploid offspring, the cross performed in Cage 3 produced unexpected offspring of varying ploidy. While the inventors do not wish to be bound by any theory, it is believed that the variation in the offspring may be due to the genetics of either of the parents involved in the cross.

Example 2

Production of Viable Seeds from Triploid Apomictic *P. argentatum* Plant in the Presence of a Fertile Pollen Source This Example illustrates methods for promoting the production of viable seeds from an apomictic guayule plant in accordance with at least some alternatives of the present disclosure.

Two genetically identical triploid *P. argentatum* plants and two tetraploid *P. argentatum* plants were grown under standard greenhouse conditions until flowering. One of the triploid plants was grown in isolation and allowed to self-pollinate to produce selfed-seeds. The other triploid plant was spatially isolated from the first triploid plant and was grown alongside with the two tetraploid plants. Achenes were harvested from each of the triploid plants after thirty days of isolated growth. The achenes were then germinated on a paper towel in a 15 cm petri dish with 20 ml of $diH_2O$. The petri dishes were sealed with parafilm and incubated in a growth chamber with a 14 hour day length, day temperature of 27° C. and night temperature of 22° C. The number of germinated seeds was scored at day 4, day 7, and day 14 of incubation. Seedling survival scores were revisited at day 35 of incubation. The results of this germination study are summarized in TABLE 3.

TABLE 3

Germination counts, percentages, and survival rates of the two geographically isolated crosses

| Cross | Achenes Collected From | Number of Achenes Collected | Number of Achenes Germinated | | | Percent Germination | | | Seedling Survival @ Day 35 | |
|---|---|---|---|---|---|---|---|---|---|---|
| | | | Day 4 | Day 7 | Day 14 | Day 4 | Day 7 | Day 14 | Number | Percent |
| 3X × 4X | 3X | 54 | 7 | 14 | 16 | 12.9 | 25.9 | 29.6 | 12 | 75 |
| 3X selfed | 3X | 66 | 0 | 3 | 6 | 0 | 4.5 | 9.1 | 0 | 0 |

Seedlings resulting from the pollination of the triploid plant with pollen from a tetraploid showed a 75% survival rate at 35 days. In contrast, the seedlings resulting from the selfing of a genetically identical triploid plant showed no survival, indicating that fertile pollen is necessary to produce viable offspring from triploid plants. Although six seedlings from the selfing of the second triploid plant did initially germinate, none survived beyond just a few days and each was observed to display abnormal growth patterns. Without being bound to any particular theory, it may well be that the development of embryo and/or endosperm did not complete in these seeds. This germination study indicates that the presence of fertile pollen is needed to produce viable seed from triploid apomictic guayule.

Example 3

Interspecific Pollination Promotes Production of Viable Seeds from Apomictic Pentaploid *Parthenium argentatum*

This Example illustrates methods in accordance with at least some alternatives of the present disclosure, in which fertile pollen of mariola (*P. incanum*) can be used as a pollen donor for the production of viable seeds from an apomictic *P. argentatum* plant.

A mariola plant and pentaploid guayule plant were grown under standard greenhouse conditions until flowering. The plants was pruned of flowers and placed together in a pollination cage. Blue bottle flies (genus *Calliphora*) were added weekly to the cages to facilitate pollination. Achenes were harvested from the guayule plant after thirty days of co-cultivation. The achenes were then germinated on a paper towel in a 15 cm petri dish with 20 ml of diH$_2$O. The petri dish was sealed with parafilm and incubated in a growth chamber with a 14 hour day length, day temperature of 27° C. and night temperature of 22° C. for germination. The number of germinated seeds was scored at day 4, day 7, and day 14. Seedling survival was revisited at day 35 of incubation. The results of this germination study are summarized in TABLE 4. Remarkably, 7.5% of the seeds germinated and of these, 58.3% of the seedlings derived from the interploidy crosses germinated and survived after 35 days of incubation.

TABLE 4

Germination counts, percentages, and survival rates of F1 hybrids of the two caged crosses

| Location | Cross | Achenes Collected From | Number of Achenes Collected | Number of Achenes Germinated | | | Percent Germination | | | Seedling Survival @ Day 35 | |
|---|---|---|---|---|---|---|---|---|---|---|---|
| | | | | Day 4 | Day 7 | Day 14 | Day 4 | Day 7 | Day 14 | Number | Percent |
| CAGE 7 | 5X × Mariola | 5X | 159 | 0 | 9 | 12 | 0 | 5.7 | 7.5 | 7 | 58.3 |

Figures 4, 5:
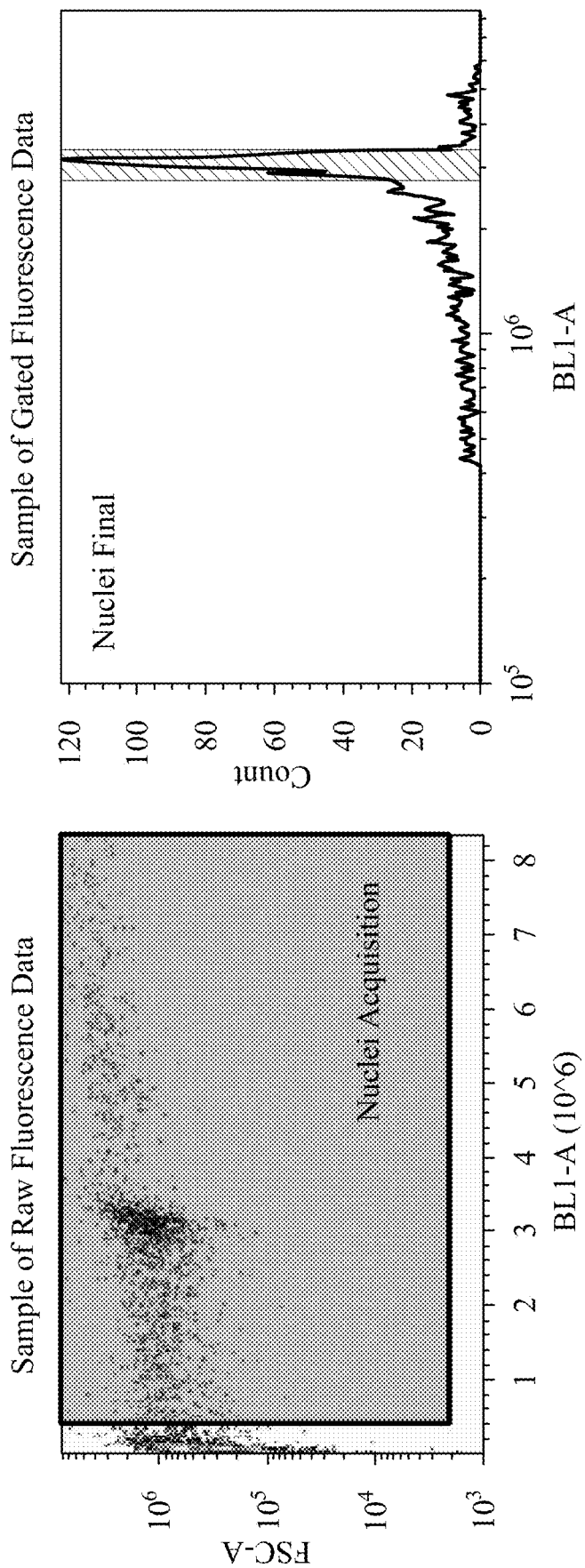
FIG. 4: Events recorded by the flow cytometer plotted by forward scatter (y-axis) and DNA fluorescence (x-axis). A nuclei gate is used to remove background debris from further analysis.
FIG. 5: Histogram of fluorescence values from gated events in FIG. 4. The gate gives the median fluorescence value for nuclei in the sample.

After the F1 seedlings were fully established in 4-inch pots, two 5-mm hole punches were sampled from each seedling in triplicate and placed into a 96-well microtube rack. Tissue was also collected from plants of diploid, triploid, and tetraploid plant controls and loaded on the microtube rack. Ploidy levels of the hybrid seedlings were determined by using the same procedure described in Example 1 above. Nuclei peaks were manually gated (FIGS. 4 and 5) and resulting median fluorescence values were compared against intraspecific controls to generate ploidy callus.

Figure 6:
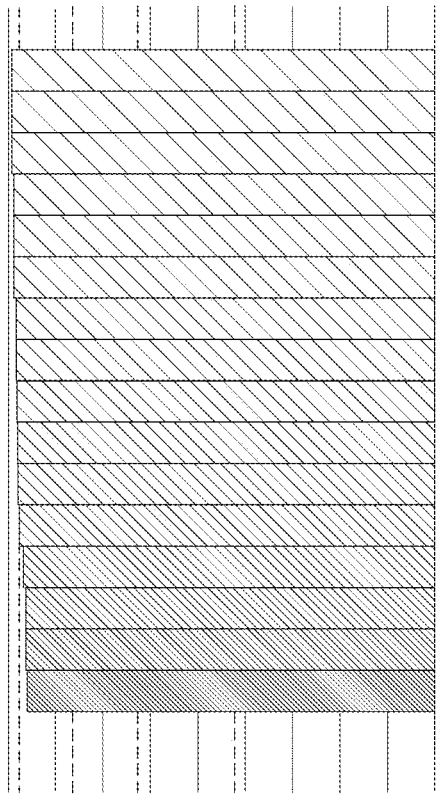
FIG. 6: Fluorescence of intraspecific guayule controls (2×, 3×, 4× from left to right). Dotted lines correspond to median fluorescent values for each ploidy level.
Figure 7:
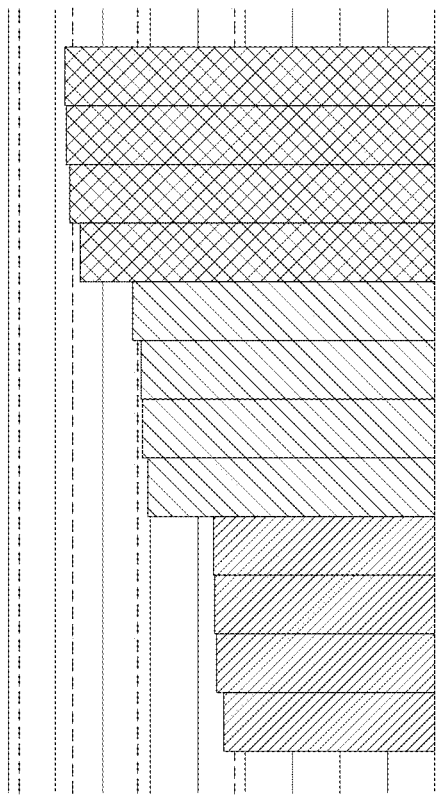
FIG. 7: Fluorescence of F1 seedlings resulting from the pollination of a pentaploid guayule by a mariola plant. Dotted lines correspond to median fluorescent values for each ploidy level.

The F1 seedling fluorescence data (FIG. 7), when compared against intraspecific controls (FIG. 6), indicates that all six F1 seedlings were pentaploids.

CONCLUSIONS

As previously shown, and described in Example 2 above, hybrid guayule requires a source of fertile pollen to produce viable seeds. In Example 3, seeds were germinated from a cross between guayule and mariola, and the experiments showed that seedlings derived from these hybrid seeds were viable. The results indicated that mariola could be used as a pollen donor to produce viable guayule seeds from apomictic pentaploid plants.

Subsequent cytometric analysis revealed that these hybrid seedlings were all pentaploid, indicating that they were apomictic progeny of the mother pentaploid plant. Additionally, these seedlings displayed no phenotypic features characteristics of interspecific hybrids. These plants are expected to have been produced apomictically, which can be verified by Genotyping-by-Sequencing.

Comparative experiments with diploid and tetraploid mariola used as pollen donors are contemplated so as to determine which ploidy will be most effective as a pollinator. Additionally, it is contemplated that one can produce higher seed counts from these interploidy and/or interspecific crosses so as to increase the probability of producing interspecific off-types resulting from the fertilization of the guayule embryo by mariola pollen, as this may help to validate the approach of culling by interspecific phenotype during seed multiplication. It is further contemplated that one can produce higher seed counts from these interploidy and/or interspecific crosses so as to increase the rate of seed increase.

Although initially mariola was used as a pollinator because it is the most closely related species to guayule, the methods described herein can be used with any of the 14 other species in the *Parthenium* genus as pollinators.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A method for promoting the production of viable hybrid guayule seeds from an interploidy cross, said method comprising:
   selecting a female guayule plant and a pollinator plant, wherein said female guayule plant is a triploid that reproduces apomictically and said pollinator plant is a tetraploid guayule plant capable of producing fertile pollen;
   pollinating said female guayule plant with pollen from said pollinator plant to produce triploid hybrid seeds on said female guayule plant, wherein at least 5% of said triploid hybrid seeds have germinated and will survive 35 days after incubation.

2. The method of claim 1, wherein said female guayule plant and said pollinator plant belong to the *Parthenium argentatum* species.

3. The method of claim 1, wherein at least one of said female guayule plant or said pollinator plant is pre-selected for enhanced plant productivity.

4. The method of claim 1, wherein at least one of said female guayule plant or said pollinator plant is clonally propagated prior to pollination step.

5. The method of claim 1, wherein said percentage of seeds germinated is scored at 7 days after incubation.

6. The method of claim 1, wherein at least 20% of said triploid hybrid seeds have germinated at 14 days after incubation.

7. The method of claim 6, wherein at least 35% of said seeds germinated at 14 days after incubation survive 35 days after incubation.

8. A method for promoting the production of viable hybrid guayule seeds from an interploidy cross, said method comprising:
    selecting a female guayule plant and a pollinator plant, wherein said a female guayule plant is a pentaploid that reproduces apomictically and said pollinator plant is capable of producing fertile pollen;
    pollinating said female guayule plant with pollen from said pollinator plant to produce pentaploid seeds on said female guayule plant, wherein at least 5% of said pentaploid seeds that germinated within 14 days after incubation survive at least 35 days after incubation.

9. The method of claim 8, wherein said pollinator plant is a mariola plant.

10. The method of claim 8, wherein said female guayule plant and said pollinator plant belong to the *Parthenium argentatum* species.

11. The method of claim 8, wherein said pollinator plant belongs to a different *Parthenium* species than said female guayule plant.

12. The method of claim 8, wherein the pollinator plant is of a species selected from the group consisting of *P. alpinum, P. argentatum, P. cineraceum, P. confertum, P. fruticosum, P. hysterophorus, P. incanum, P. integrifolium, P. ligulatum, P. rollinsianum, P. schottii*, and *P. tomentosum*.

13. The method of claim 8, wherein said pollinator plant is a *Parthenium argentatum* plant.

14. The method of claim 8, wherein said pollinator plant is a *Parthenium incanum* plant.

15. The method of claim 8, wherein at least one of said female guayule plant or said pollinator plant is pre-selected for enhanced plant productivity.

16. The method of claim 8, wherein at least one of said female guayule plant or said pollinator plant is clonally propagated prior to pollination step.

17. The method of claim 8, wherein said pollinator plant is of a *Parthenium* species that is different than *Parthenium argentatum* such that any F1 hybrid off-types from said interploidy cross can be conveniently identified.

18. The method of claim 8, wherein said percentage of germinated seeds is scored at 14 days after incubation.

19. The method of claim 18, wherein at least 55% of said pentaploid seeds that germinated at 14 days after incubation survive at least 35 days after incubation.

* * * * *